United States Patent [19]

Urquhart

[11] 3,991,759
[45] Nov. 16, 1976

[54] METHOD AND THERAPEUTIC SYSTEM FOR TREATING AQUEOUS DEFICIENT DRY EYE

[75] Inventor: John Urquhart, Palo Alto, Calif.
[73] Assignee: Alza Corporation, Palo Alto, Calif.
[22] Filed: Oct. 28, 1975
[21] Appl. No.: 625,918

[52] U.S. Cl. .................................... 128/260; 128/249
[51] Int. Cl.² ..................... A61M 7/00; A61M 31/00
[58] Field of Search ............ 128/260, 272, 249, 233; 424/19, 22, 33

[56] References Cited
UNITED STATES PATENTS

| | | | |
|---|---|---|---|
| 3,664,340 | 5/1972 | Morgan | 128/249 |
| 3,811,444 | 5/1974 | Heller | 128/260 |
| 3,818,909 | 6/1974 | Braton | 128/232 |
| 3,828,777 | 8/1974 | Ness | 128/260 |
| 3,832,458 | 8/1974 | Merrill | 424/19 |
| 3,896,819 | 7/1975 | Zaffaroni | 128/130 |
| 3,917,119 | 11/1975 | Kahn | 128/249 X |

OTHER PUBLICATIONS

*New Concepts In Ocular Xerosis,* Dohlman C. H., Trans. Opthal. Society, UK 91, 105–117 (1971).

*Tear Substitutes in the Treatment of Dry Eyes,* Lemp, M. A. Int. Opthal. Clin. 13, 145–153 (1973).

*Primary Examiner*—Aldrich F. Medbery
*Attorney, Agent, or Firm*—Thomas E. Ciotti; Paul L. Sabatine; Edward L. Mandell

[57] ABSTRACT

Method for treating aqueous deficient dry eye by instilling a biologically compatible solute, such as sodium chloride, into the tear film continuously at a controlled rate that is sufficient to osmotically induce a continuous flow of water from the interstitial fluid to the tear film and thereby correct the aqueous deficiency. The method may be carried out by placing a therapeutic system, in the form of an ocular insert, into the cul-de-sac, the insert comprising the solute confined within a polymer matrix that releases the solute continuously at 3 to 20 micromoles of solute species per hour.

21 Claims, No Drawings

METHOD AND THERAPEUTIC SYSTEM FOR TREATING AQUEOUS DEFICIENT DRY EYE

BACKGROUND OF THE INVENTION

1. Field of the Invention

This invention relates to a therapeutic system, in the form of an ocular insert, and to a method for treating aqueous deficient dry eye.

2. Description of the Prior Art

The term "dry eyes" is used to denote a multitude of ophthalmic conditions that manifest themselves in common symptoms ranging from slight irritation to incapacitating discomfort and blindness from corneal damage. These conditions have been divided by causation into two categories: those caused by aqueous deficiency, both congenital and acquired, and those caused by mucin deficiency. The aqueous deficient dry eye is characterized by insufficient aqueous tear production to maintain a stable tear film; whereas the mucin deficient eye is characterized by instability of the tear film despite adequate aqueous tear production. The present invention relates to the aqueous deficient dry eye.

*New Concepts In Ocular Xerosis*, Dohlman, C. H., Trans. Ophthal. Soc. U.K. 91, 105–117 (1971), and *Tear Substitutes in the Treatment of Dry Eyes*, Lemp. M. A. Int. Ophthal. Clin. 13, 145–153 (1973) give excellent reviews of the available therapy for treating aqueous deficient dry eyes. As reported by Lemp, the treatment of aqueous deficient dry eyes has been limited primarily to using artificial tears to periodically supplement inadequate production of tears. Isotonic saline drops were used initially as artificial tears but were found to provide only short-lived relief. Also, they have to be instilled on the order of three to twelve times a day depending upon the severity of the condition. In order to prolong relief, water soluble polymers have been added to the isotonic saline solution to make it more viscous. In this regard, artificial tear solutions containing methyl cellulose, methyl cellulose derivatives, ethyl cellulose, polyvinyl alcohol and/or other soluble polymers are commercially available. However, it is reported that even these more viscous solutions provide only short-lived relief and do not remain in contact with the cornea for longer than 15 minutes after instillation.

Hydrophilic ("soft") contact lenses used in conjunction with artificial tears have been used to treat aqueous deficient dry eyes. However, such treatment has been experimental and also requires frequent instillation of artificial tear solution. Dohlman, supra, has also suggested that constant rate delivery of small amounts of fluid would be more desirable than using artificial tear drops in the case of severe cases of aqueous deficient eyes. Specifically, he describes a system that delivers 1–3 ml/hr of solution to the eye on a continuous basis involving a small pump that is connected to tubing that in turn is attached to spectacle frames and extends into the sac of the eye.

*Potential Use of Ocular-Insert Therapy in Dry Eyes*, Pavan-Langston, D., Int. Ophthal. Clin. 13, 231–238 (1973) discusses the potential use of ocular inserts to treat dry eyes. It concludes that ocular inserts are not good candidates for treating aqueous deficient dry eyes, but that they might be used to treat mucin deficient dry eyes.

SUMMARY OF THE INVENTION

The invention is the result of the concept that continuous therapy for aqueous deficient dry eyes may be realized by continuously adding an appropriate solute to the tear film at a rate that induces sufficient osmotic flow of water from the interstitial fluid surrounding tissue, primarily the conjunctiva, to the tear film to remedy the deficiency. Accordingly, the invention takes the form of a therapeutic system, namely an ocular insert, and a method for treating aqueous deficient dry eyes continuously for prolonged time periods.

The invention method comprises administering a biologically compatible solute to the tear film continuously for a prolonged time period at a controlled rate that is sufficient to osmotically induce continuous endogenous aqueous flow to the tear film at a rate that is therapeutically effective. The invention ocular insert comprises said solute confined within a polymer body that is sized and shaped for insertion and retention in the cul-de-sac of the eye and that, when inserted in the eye, releases the solute continuously for a prolonged time period at a controlled rate that is sufficient to osmotically induce continuous endogenous aqueous flow to the tear film at a rate that is therapeutically effective.

DETAILED DESCRIPTION OF THE INVENTION

Inserts of varying structure and operation may be used in the invention to dispense solute to the tear film. These inserts have the common features that they all comprise the solute confined within a polymer body, and all are sized and shaped to be inserted and retained comfortably within the cul-de-sac of the eye. Depending on the particular solute to be dispensed, the insert may operate by either a diffusion mechanism or an osmotic mechanism. Inserts that operate on an osmotic mechanism may be adaptations of the osmotically driven dispensers described in commonly owned U.S. Pat. No. 3,845,770 and Belgian Pat. Nos. 778,005 (corresponds to U.S. Ser. No. 106,161 filed Jan. 13, 1971) and 314,123 (corresponds to U.S. Ser. No. 354,359 filed Apr. 25, 1973). Inserts made in accordance with Belgian Pat. No. 778,005 will comprise the solute formulated as a dispensible fluid, such as a gel or a paste, in one of the osmotic dispensers described in the patent. Inserts made pursuant to U.S. Pat. No. 3,845,770 will comprise the solute confined within a polymeric wall of controlled permeability to water that has one or more specifically sized outlets in it. And, inserts of the type described in Belgian Pat. No. 314,123 will comprise discrete depots of the solute dispersed in a polymer matrix as described in the patent.

Solutes that are capable of diffusing through polymer membranes, such as certain nonionic solutes, may be dispensed from either reservoir-type or monolithic dispersion-type diffusion dispensers, such as those described in U.S. Pat. No. 3,618,604. In all instances, the structure and composition of the insert must be such that it continuously dispenses solute at a rate that provides therapy to the aqueous deficient dry eye.

Solutes that are dispensed from the above-described inserts pursuant to the invention method are those that are (a) capable of causing sufficient osmotic flow of water from the interstitial fluid to the tear film to provide the desired therapy, and (b) are biologically compatible with the eye in the sense that they are not inherently harmful or substantially irritating to the eye at the dosages at which they are administered, and have no significant topical or systemic pharmacological or physiological effects at the dosages at which they are administered, other than to induce aqueous flow in accordance with the invention. The ability of the solute to induce such flow will depend upon the solubility of the solute in the tear film, and its ionic structure, and the rate at which the solute is absorbed or otherwise transported by eye tissues and/or surrounding tissue. The mobility (capacity to be transported from the tear film) of the solute may be expressed in terms of its osmotic reflection coefficient, with the coefficient being unity if there is no solute mobility and zero if the mobility of the solute equals that of the solvent. The solute should have a tear film solubility of at least 1% by weight and not be rapidly absorbed by, or otherwise transported through, eye tissue and/or surrounding tissue. Preferably, the osmotic reflection coefficient is above about 0.7. Also, the amount of solute repaired to provide therapy is dependent upon the solute's molecular weight, since osmotic pressure is dependent upon the molal concentration of the solute in the tear film. Because of this, solutes of relatively low molecular weight, that is less than about 500, are preferred. Examples of solutes that may be used are: inorganic salts, particularly salts of alkali metals or alkaline earth metals, such as sodium chloride, magnesium sulfate, magnesium chloride, potassium sulfate, sodium carbonate, sodium sulfite, calcium bicarbonate, sodium sulfate, calcium sulfate, and potassium acid phosphate; organic salts, particularly the alkali metal or alkaline earth metal salts of fatty acids, such as calcium lactate, magnesium succinate and sodium succinate; and sugars such as lactose, fructose, dextrose, sucrose and mannitol. Mixtures of such solutes may be used if desired. The amount of solute in the insert will be limited by the maximum size of the insert. Within this limitation, it will also depend upon the desired therapeutic lifetime of the insert and the factors discussed above. The inserts will usually contain sufficient solute to provide therapy for at least an hour and normally for about 1 hr to about 4 days. For such therapy periods, the inserts will contain between about 2 and 75 mg of solute.

Polymers that may be used to make the ocular inserts are described in the above-mentioned U.S. and Belgian patents. The techniques for making the inserts are likewise described in said patents. In addition to the polymer and solute, the inserts may include other materials such as antioxidants, pigments, surfactants, plasticizers, and the like.

The dry eye therapy realized by the invention method is achieved by supplementing the aqueous content of the tear film with water imbibed from the interstitial fluid of the surrounding tissue, such as the conjunctiva. This inhibition occurs because of the effect of the continuous addition of solute to the tear film on the osmotic equilibrium between the two sides of the mucous membranes that constitute the palpebral and bulbar conjuctivae and the tendency to maintain osmotic equilibrium between the two sides of those membranes. The implied loss of water from the interstitial fluid will be compensated for by exchange of water from the underlying capillaries to the interstitial fluid. In most cases therapy will be achieved by increasing the aqueous tear production at least about 50 percent, preferably 100 to 300 percent, above normal. Greater increases than these may be therapeutic but may result in the increased tear production running out of the eyes. Also, the quantity of solute added to the tear film to achieve such greater increases may cause intolerable irritation of the eye. In theory, the addition of about 0.3 mole of solute species will induce the flow of about one liter of water. (As used herein "solute species" means the molecular or ionic moieties that exist when the solute dissolves. For ionic solutes, the solute species are the dissociated ions that exist after the solute dissociates. For example, in the case of sodium chloride, the dissolution of one mole of sodium chloride will create two moles of solute species, namely one mole of sodium ion and one mole of chloride ion. For nonionic solutes, the solute species will be the undissociated molecules of solute.) This may be correlated to the tear volume to determine the approximate rate at which solute should be added to the tear flow to increase tear production to a therapeutic level. It should, of course, be realized that the actual flow of water induced by the solute may deviate from the theoretical flow because of reflex lacrimation caused by the presence of a foreign body (the insert and solute) in the eye and the mobility of the solute. Reflex lacrimation will increase the flow and solute mobility will decrease the flow. In most instances, solute dosages of about 3 to about 20 micromoles solute species per hour will be therapeutic. For the preferred solute, sodium chloride, this is equivalent to about 100 to about 600 mcg/hr. Preferably, the rate of solute instillation is substantially constant.

EXAMPLES

The following examples illustrate the inserts and method of the invention. These examples are not intended to limit the invention in any manner. Proportions are by weight unless indicated otherwise.

EXAMPLE 1

Preparation of Inserts

Adaptations of the inserts described in Belgian Pat. No. 314,123 were prepared as follows: a mixture of 64% ethylene-vinyl acetate copolymer (40% vinyl acetate, sold under the trade designation ELVAX 40), 1% nonionic surfactant (sold under the trade designation TWEEN 20), and 35% NaCl (G95-TCP from Diamond Crystal Salt Co., 95% < 40 microns) was blended on the rollers of a small rubber mill. The mixture was then melt pressed at 57° C, 13,600 kg pressure for 5 minutes into a sheet approximately 330 microns thick. Inserts of varying size and shape were cut from the film. The inserts were washed in water at ambient temperature for 3 hours.

Determination of In Vitro NaCl Release Rate

Representative specimens of the inserts were suspended in a known volume of isotonic glycerin (2.6% by weight) solution at 37° C and vertically reciprocated therein. NaCl concentration of the solution was measured periodically by specific conductance and atomic absorption spectrophotometry. Average NaCl release rates were calculated from those measurements.

In Vivo Tear Flow Test

New Zealand white rabbits, 2–3 kg, that had been delacrimated and had Harder's gland blocked, were used. A saline-filled 4 cm, 13 gauge catheter was inserted through an incision in the cheek and into the lacrimal sac of each rabbit. An electrode was imbedded in the eyelid to stimulate blinking every 5 sec. Basal tear flow was measured by weighing the fluid that drained from the catheter over 0–30 min. After the initial 30 min., an insert was placed in the eye and tear flow over four succeeding 20 min. periods was measured as above. From these four measurements a mean flow increment (the increase in flow over basal flow) was calculated.

Details on the sizes and shapes of the inserts, their in vitro release rates, and the results of the tear flow tests are reported in Table 1 below:

Modifications of the above-described inserts and methods that are obvious to those of skill in the chemical, pharmaceutical, and/or medical arts are intended to be within the scope of the following claims.

We claim:

1. Method for treating an aqueous deficient dry eye comprising instilling a biologically compatible solute in the tear film of said eye continuously for a prolonged time period at a controlled rate that is sufficient to osmotically induce continuous emdogenous aqueous

TABLE 1

| Insert Shape | Surface Area (cm²) | In Vitro NaCl Release Rate (Mcg/hr) | Rabbit No. | Basal Tear Flow (mcl/min) | Mean Tear Flow (mcl/min) Increment During Continuous NaCl Delivery from Insert |
|---|---|---|---|---|---|
| Half Crescent | 0.5 | 250 | 1 | 38 | 16 |
| Half Crescent | 0.5 | 250 | 2 | 33 | 20 |
| Half Crescent | 0.5 | 250 | 3 | 44 | 36 |
| Half Crescent | 0.5 | 250 | 4 | 34 | 26 |
| Half Crescent | 0.5 | 250 | 5 | 60 | 69 |
| Half Crescent | 0.5 | 250 | 6 | 11 | 65 |
| Half Crescent | 0.5 | 250 | 7 | 13 | 27 |
| Half Crescent | 0.5 | 250 | 8 | 27 | 44 |
| Half Crescent | 0.5 | 250 | 9 | 33 | 42 |
| | | | | Avg. 33 | Avg. 38 |
| Crescent | 1.0 | 500 | 10 | 12 | 41 |
| Crescent | 1.0 | 500 | 11 | 34 | 86 |
| Crescent | 1.0 | 500 | 12 | 19 | 50 |
| Crescent | 1.0 | 500 | 13 | 68 | 37 |
| | | | | Avg. 33 | Avg. 54 |
| Ellipse | 1.25 | 630 | 14 | 40 | 38 |
| Ellipse | 1.25 | 630 | 15 | 26 | 56 |
| Ellipse | 1.25 | 630 | 16 | 8 | 54 |
| Ellipse | 1.25 | 630 | 17 | 23 | 48 |
| Ellipse | 1.25 | 630 | 18 | 73 | 86 |
| Ellipse | 1.25 | 630 | 19 | 20 | 61 |
| Ellipse | 1.25 | 630 | 20 | 38 | 50 |
| Ellipse | 1.25 | 630 | 21 | 17 | 51 |
| Ellipse | 1.25 | 630 | 22 | 13 | 55 |
| Ellipse | 1.25 | 630 | 23 | 21 | 44 |
| Ellipse | 1.25 | 630 | 24 | 11 | 70 |
| | | | | Avg. 26 | Avg. 56 |

The data of Table 1 show that aqueous tear production can be increased significantly by using the inserts of the invention. In this regard, the average increases in tear flow over basal tear flow effected by the 250, 500, and 630 mcg/hr inserts were 115, 164, and 215 percent, respectively.

EXAMPLE 2

Preparation of Inserts

Adaptations of the inserts described in U.S. Pat. No. 3,845,770 were prepared as follows: 90 g sodium chloride was mixed with a solution of 10 g ethylene-vinyl acetate copolymer (40% by weight vinyl acetate, sold under the trade designation Elvax 40) in 90 g methylene chloride and the mixture was allowed to dry for approximately one day. The dried mixture was then milled and formed into a 0.8 mm thick sheet. Elliptical units 13.5 × 5.8 mm were cut from the sheet.

The above units were coated with a 70 micron thick coating of cellulose acetate butyrate (17% by weight butyryl) in a Wooster coating apparatus and a single 175 micron diameter hole was drilled through the coating of each unit using a $CO_2$ laser.

Determination of In Vitro NaCl Release Rate

Determinations were made by the procedure of Example 1. After about 1½ hr the average release rate reached about 950 mcg/hr. It remained substantially constant at that level of approximately the next 46 hr and then began to decrease slowly.

flow to the tear film during said period at a rate that increases aqueous tear production to a therapeutically effective level.

2. The method of claim 1 wherein said controlled rate is substantially constant.

3. The method of claim 1 wherein said controlled rate is in the range of about 3 to about 20 micromoles of solute species per hour.

4. The method of claim 1 wherein said time period is in the range of about 1 hr to about 4 days.

5. The method of claim 1 wherein the solute has a tear film solubility of at least 1% by weight and is not rapidly absorbed by or transported through eye tissue and/or tissue surrounding the eye.

6. The method of claim 5 wherein the osmotic reflection coefficient of the solute is above about 0.7.

7. The method of claim 1 wherein the solute is an inorganic salt of an alkali metal or alkaline earth metal, an alkali metal or alkaline earth metal salt of a fatty acid, or a sugar.

8. The method of claim 7 wherein the molecular weight of the solute is less than about 500.

9. The method of claim 1 wherein said solute is sodium chloride.

10. The method of claim 9 wherein said controlled rate is 100 to 600 mcg/hr.

11. The method of claim 1 wherein the solute is sodium chloride, the prolonged period of time is about 1 hr to about 4 days, and the controlled rate is 100 to 600 mcg/hr.

12. The method of claim 11 wherein the controlled rate is substantially constant.

13. A therapeutic system in the form of an ocular insert for treating an aqueous deficient dry eye comprising a biologically compatible solute confined within a polymer body that is sized and shaped for insertion and retention in the cul-de-sac of the eye, said system when inserted in the eye, comprising a means for releasing the solute continuously for a prolonged time period at a controlled rate that is sufficient to induce continuous endogenous agueous flow to the tear film during said period at a rate that is therapeutically effective.

14. The insert of claim 13 wherein the total amount of solute in the insert is sufficient to release said solute at said controlled rate for about 1 hr to about 4 days.

15. The insert of claim 14 wherein the total amount of solute in the insert is 2 to 75 mg.

16. The insert of claim 13 wherein said controlled rate is in the range of about 3 to about 20 micromoles of solute species per hour.

17. The insert of claim 13 wherein the solute has a tear film solubility of at least 1% by weight and is not rapidly absorbed by or transported through eye tissue and/or tissue surrounding the eye.

18. The insert of claim 17 wherein the osmotic reflection coefficient of the solute is above about 0.7.

19. The insert of claim 13 wherein the solute has a molecular weight less than 500 and is an inorganic salt of an alkali metal or alkaline earth metal, an alkali metal or alkaline earth metal salt of a fatty acid, or a sugar.

20. The insert of claim 13 wherein the solute is NaCl.

21. The insert of claim 20 wherein said controlled rate is 100 to 600 mcg/hr.

* * * * *